US010702175B2

(12) United States Patent
Chang et al.

(10) Patent No.: US 10,702,175 B2
(45) Date of Patent: Jul. 7, 2020

(54) BRAIN ACTIVITY ANALYSIS METHOD AND APPARATUS THEREOF

(71) Applicant: A-NEURON ELECTRONIC CORP., Zhubei (TW)

(72) Inventors: Chia-Chi Chang, Taipei (TW); Pei-Chen Lin, Hsinchu (TW)

(73) Assignee: A-Neuron Electronic Corp., Hsinchu (TW)

( * ) Notice: Subject to any disclaimer, the term of this patent is extended or adjusted under 35 U.S.C. 154(b) by 343 days.

(21) Appl. No.: 15/642,510

(22) Filed: Jul. 6, 2017

(65) Prior Publication Data

US 2018/0317792 A1 Nov. 8, 2018

(30) Foreign Application Priority Data

May 4, 2017 (TW) .............................. 106114720 A

(51) Int. Cl.
*A61B 5/04* (2006.01)
*A61B 5/0476* (2006.01)
(Continued)

(52) U.S. Cl.
CPC .......... *A61B 5/04012* (2013.01); *A61B 5/048* (2013.01); *A61B 5/0476* (2013.01);
(Continued)

(58) Field of Classification Search
CPC ........... A61B 5/04012; A61B 5/04014; A61B 5/04015; A61B 5/04017; A61B 5/04018;
(Continued)

(56) References Cited

U.S. PATENT DOCUMENTS 6,480,743 B1 11/2002 Kirkpatrick et al.
6,810,285 B2 10/2004 Pless et al.
(Continued)

FOREIGN PATENT DOCUMENTS

| CN | 101810479 A | 8/2010 |
| CN | 102824173 B | 4/2014 |
| TW | 1487503 B | 6/2015 |

OTHER PUBLICATIONS

Chang, et al. (Nov. 2011). On-line empirical mode decomposition biomedical microprocessor for Hilbert Huang transform. In 2011 IEEE Biomedical Circuits and Systems Conference (BioCAS) (pp. 420-423). IEEE. (Year: 2011).*

(Continued)

*Primary Examiner* — David J. McCrosky
(74) *Attorney, Agent, or Firm* — Rosenberg, Klein & Lee

(57) ABSTRACT

The present invention discloses a brain activity analysis method and apparatus, which is based on a nonlinear waveform decomposition technology, wherein the changes of the intrinsic features in brain waves are decomposed and demodulated to extract the modulation signals of the components, including the frequency-modulation signals and the amplitude-modulation signals. The present invention further uses a feature mask to determine whether to proceed further decomposition and demodulation of the extracted modulation signals. If not, the multidimensional changes of the intrinsic features are obtained according to the feature mask. Then, quantitation and identification is performed to obtain the status of brain function. The present invention not only effectively increases the accuracy of the identification but also uses the feature mask to obviously reduce the complexity and the load of computation.

9 Claims, 13 Drawing Sheets

(51) Int. Cl.
  *A61B 5/00* (2006.01)
  *G16H 50/20* (2018.01)
  *A61B 5/048* (2006.01)
  *G16H 40/63* (2018.01)

(52) U.S. Cl.
  CPC .......... *A61B 5/4094* (2013.01); *A61B 5/7228* (2013.01); *A61B 5/7264* (2013.01); *A61B 5/7282* (2013.01); *A61B 5/742* (2013.01); *G16H 40/63* (2018.01); *G16H 50/20* (2018.01)

(58) Field of Classification Search
  CPC ..... A61B 5/0476; A61B 5/048; A61B 5/0482; A61B 5/0484; A61B 5/04842; A61B 5/04845; A61B 5/04847
  See application file for complete search history.

(56) References Cited

U.S. PATENT DOCUMENTS

| | | |
|---|---|---|
| 8,131,352 B2 | 3/2012 | Greene |
| 2006/0111644 A1 | 5/2006 | Guttag et al. |

OTHER PUBLICATIONS

Zhang Pengbo et al., Adaptive Detection Method Based on Instantaneous Bandwidth Feature for Seizure Onset, Chinese Journal of Scientific Instrument, vol. 37, No. 6, Jun. 2016.

Zhu Yong et al., An EMD Based Epileptic Spike Detection Method, Journal of Biomedical Engineering, vol. 25, No. 2, Apr. 2008.

Varun Bajaj, Ram Bilas Pachori, "Classification of Seizure and Nonseizure EEG Signals Using Empirical Mode Decomposition", IEEE Transactions on Information Technology in Biomedicine (vol. 16, Issue: 6, Nov. 2012), pp. 1135-1142.

R. Faltermeier, A. Zeiler, I. R. Keck, A. M. Tome, A. Brawanski, E. W. Lang, "Sliding Empirical Mode Decomposition", Neural Networks (IJCNN), The 2010 International Joint Conference on, Oct. 14, 2010, pp. 1-8.

Wei-Ming Chen, Herming Chiueh, Tsan-Jieh Chen, Chia-Lun Ho, Chi Jeng, Ming-Dou Ker, Chun-Yu Lin, Ya-Chun Huang, Chia-Wei Chou, Tsun-Yuan Fan, Ming-Seng Cheng, Yue-Loong Hsin, Sheng-Fu Liang, Yu-Lin Wang, Fu-Zen Shaw, Yu-Hsing Huang, Chia-Hsiang Yang, Chung-Yu Wu; A Fully Integrated 8-Channel Closed-Loop Neural-Prosthetic CMOS SoC for Real-Time Epileptic Seizure Control; IEEE Journal of Solid-State Circuits, vol. 49, No. 1, Jan. 2014, p. 232-247.

Sheng-Fu Liang, Hsu-Chuan Wang, Wan-Lin Chang; Combination of EEG Complexity and Spectral Analysis for Epilepsy Diagnosis and Seizure Detection; EURASIP Journal on Advances in Signal Processing, vol. 2010, Article ID 853434, 15 pages doi:10.1155/2010/853434.

Mark G Frei and Ivan Osorio, Intrinsic Time-Scale Decomposition: Time-Frequency-Energy Analysis and Real-Time Filtering of Non-Stationary Signals, Proc. R. Soc. A 2007 463, 321-342

* cited by examiner sub-signals with intrinsic feature $$\Sigma A_i(t)e^{jw_i(t)t}$$

BRAIN ACTIVITY ANALYSIS METHOD AND APPARATUS THEREOF

This application claims priority for Taiwan patent application no. 106114720 filed on May 4, 2017, the content of which is incorporated by reference in its entirely.

BACKGROUND OF THE INVENTION

Field of the Invention

The present invention relates to a brain wave analysis technology, particularly to a brain activity analysis method able to evaluate brain activity and an apparatus thereof.

Description of the Related Art

The conventional brain wave analysis includes waveform analysis, time-frequency analysis, complexity analysis, etc. The result of time-frequency analysis is an important reference in the related field. However, the evaluation of brain activity based on time-frequency analysis is constrained by the limitations of spectral calculation, such as the mathematic assumption, timescale resolution, information distortion, and harmonics influences. Thus, the applicability of time-frequency analysis is greatly degraded. Further, the current time-frequency analysis technology is less likely to analyze the result of multiplication but can only analyze the result of linear addition.

The conventional seizure detection, which based on time-frequency analysis method, adopts frequency measurement (by increasing a 30-40 Hz oscillation component) and amplitude measurement for seizure detection. In general, the changes of a physiological signal, such as brain electrical signal, contain various physiological mechanisms and relevant interferences. The mathematic neural network model consists of addition and multiplication within multiple layer structure. The brain wave signal is resulting from the neural network and is sensed by the electroencephalography. The conventional technology of brain wave analysis is to analyze the "features appearing in neuron operation" or the "brain function states corresponding to brain waves". However, the existing technology is hard to analyze the signal modulation of multiplication and is limited for relevant applications.

The prior art of published related patents respectively have different disadvantages. The U.S. Pat. No. 6,480,743 disclosed a "system and method for adaptive brain stimulation", which is intended to be used as a treatment of neurological diseases. The patent adopts a half-wave analysis technology to acquire the parameters for setting the waveform of the electric stimulus of treatment. The parameter setting of the prior art is mainly according to the fundamental characteristics of primitive brain wave signal. Thus, the result of identification is mainly affected by the interferences of the primitive brain wave signal. The U.S. Pat. No. 8,131,352 disclosed a "system and method for automatically adjusting detection thresholds in a feedback-controlled neurological event detector", which adopts the amplitude features of the primitive brain wave with a threshold value for the event detection. However, the amplitude features consists of various physiological information and is much sensitive to the bias of the target signal, which might cause the detection error. The U.S. Pat. No. 6,810,285 disclosed "seizure sensing and detection using an implantable device", which adopts waveform morphology analysis (including time-domain analysis and feature extraction analysis) to detect neurological events. All the operations thereof are based on the primitive waveform of the brain wave signal. Thus, the detection results are sensitive to the interferences of waveform distortion caused by noises. Further, the accuracy thereof is limited by the fact that a part of regulations of neurological functions are presented in the modulated signals and unlikely to be evaluated and estimated with the features of the primitive waveform. A Taiwan patent No. 1487503 disclosed "an automatic sleep staging device, which uses entropy analysis to evaluate the brain activity". However, the prior art cannot deal with the changes of the time-frequency features of brain wave signal but can only estimate the complexity feature. Besides, the prior art adopts the filtering and smoothing respectively before and after the main waveform processing, which might reduce the key intrinsic characteristics and practically cause detection error.

In order to evaluate brain functionality and breakthrough limitations of the conventional technology, the present invention constructs a novel algorithm to implement a brain activity analysis method and an apparatus thereof to analyze the features appearing in neuron operation and the brain function status, named brain activity, corresponding to the brain waves.

SUMMARY OF THE INVENTION

The primary objective of the present invention is to provide a brain activity analysis method and an apparatus thereof, which decomposes and analyzes frequency modulations and amplitude modulations to construct a multilayer and multidimensional feature space presenting the nonstationary features in brain activities.

Another objective of the present invention is to provide a brain activity analysis method and an apparatus thereof, which uses a feature mask to greatly reduce the computation complexity of the conventional decomposition technology and thus obviously reduce computation loading, whereby to improve the feasibility of the brain wave analysis technology.

A further objective of the present invention is to provide a brain activity analysis method and an apparatus thereof, which can improve the detection rate of the brain wave analysis.

In order to achieve the abovementioned objectives, the present invention proposes a brain activity analysis method, which comprises several steps: sensing at least one brain electrical signal; using a nonstationary decomposition method to acquire a plurality of sub-signals corresponding to intrinsic feature components; demodulating each of the sub-signals to generate modulation signals respectively corresponding to the sub-signals; undertaking recursive iterations, wherein a feature mask is used to determine whether to proceed further decomposition and demodulation of the acquired modulation signals; if yes, perform decomposition and demodulation until the iteration number, which is determined by the feature mask, has been reached; if no, i.e. the decomposition and demodulation is completed, the process directly proceeds to the next step: using the feature mask to select modulation signals of interest from all the modulation signals as feature modulation signals, and undertaking quantitation processes and identification processes of the feature modulation signals to obtain an analysis result corresponding to the brain electrical signal.

In the method of the present invention, the modulation signals include frequency-modulation parts and amplitude-modulation parts.

The present invention also proposes a brain activity analysis apparatus, which comprises at least one sensing unit, a signal processing unit, and a display unit. The sensing unit collects the brain wave signal of a subject to acquire at least one brain electrical signal. The signal processing unit is in communication with the sensing unit to receive the brain electrical signal and uses the abovementioned method to decompose and demodulate the brain electrical signal. According to a feature mask, the signal processing unit determines whether to proceed the recursive iteration of the processing or select modulation signals of interest from all the modulation signals as feature modulation signals. After acquiring the feature modulation signals, the signal processing unit performs quantitation processes and identification processes of all the feature modulation signals to obtain an analysis result corresponding to the brain electrical signal. Then, the signal processing unit presents the analysis result as brain activity on a display unit.

In one embodiment, the brain activity analysis apparatus further comprises a storage unit electrically connected with the signal processing unit to store the signals, data, and results, which are processed or generated by the signal processing unit.

Below, embodiments are described in detail in conjunction with the accompanying drawings to make easily understood the objectives, technical contents and accomplishments of the present invention.

DETAILED DESCRIPTION OF THE INVENTION

The brain activity analysis method and apparatus of the present invention is corresponding to the fundamental operation architecture of a neural network, using a nonlinear waveform decomposition technology to explore features of variations of different modulations and work out multilayer-multidimensional intrinsic variations, whereby to provide a multidimensional and low-distortion analysis technology of neurological function, wherefore the accuracy of using brain waves to diagnose neurological diseases is increased.

Figure 1:
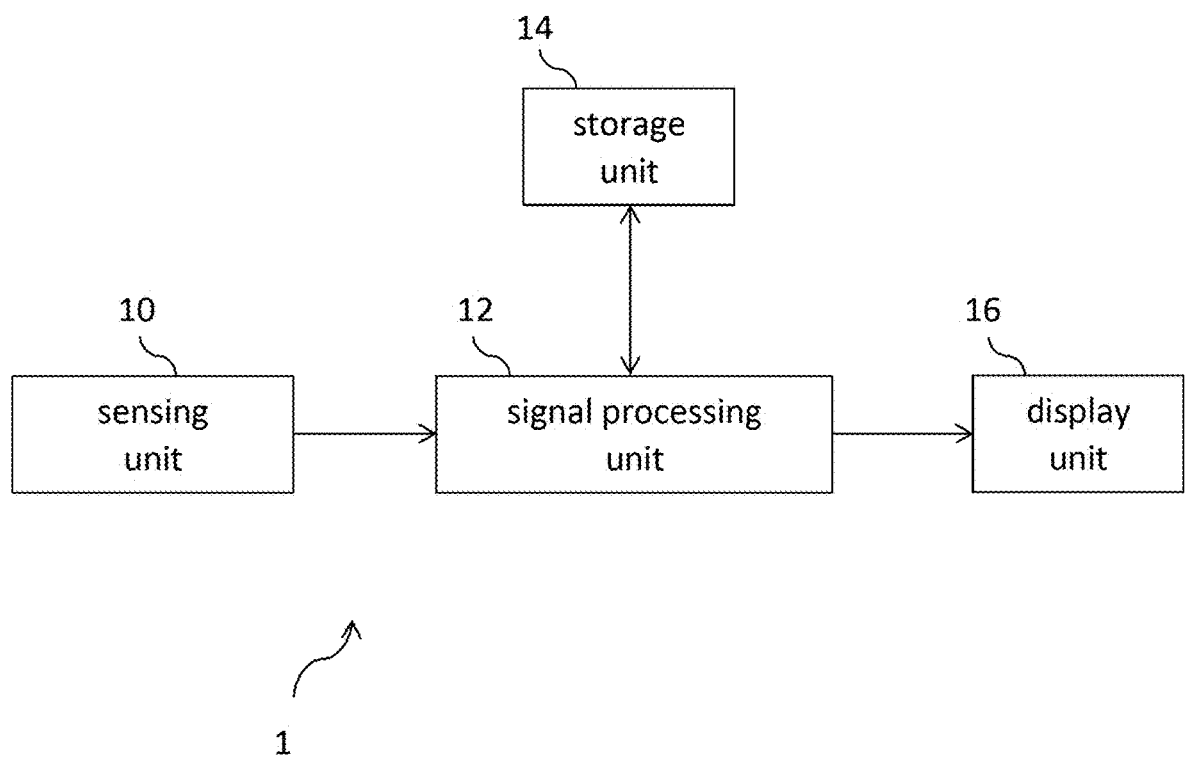
FIG. 1 is a block diagram schematically showing a brain activity analysis apparatus according to one embodiment of the present invention.

Refer to FIG. 1 a block diagram schematically showing a brain activity analysis apparatus according to one embodiment of the present invention. The brain activity analysis apparatus 1 of the present invention comprises a sensing unit 10 detecting the brain wave signal of a subject to acquire a brain electrical signal; a signal processing unit 12 in communication with the sensing unit 10; a storage unit 14 electrically connected with the signal processing unit 12; and a display unit 16 electrically connected with the signal processing unit 12. The signal processing unit 12 is an application-specific integrated circuit (ASIC), a microcontroller unit (MCU) or a microprocessor. The signal processing unit 12 receives the brain electrical signal and performs calculations of the intrinsic feature components to obtain an analysis result corresponding to the brain electrical signal, such as the status of brain activity. The models, data, and signals used in processing and analysis and the results are stored in the storage unit 14, which may be an external or built-in storage device. The display unit 16 presents the information output by the signal processing unit 12 and the results of evaluating the status of brain activity.

Figure 2:
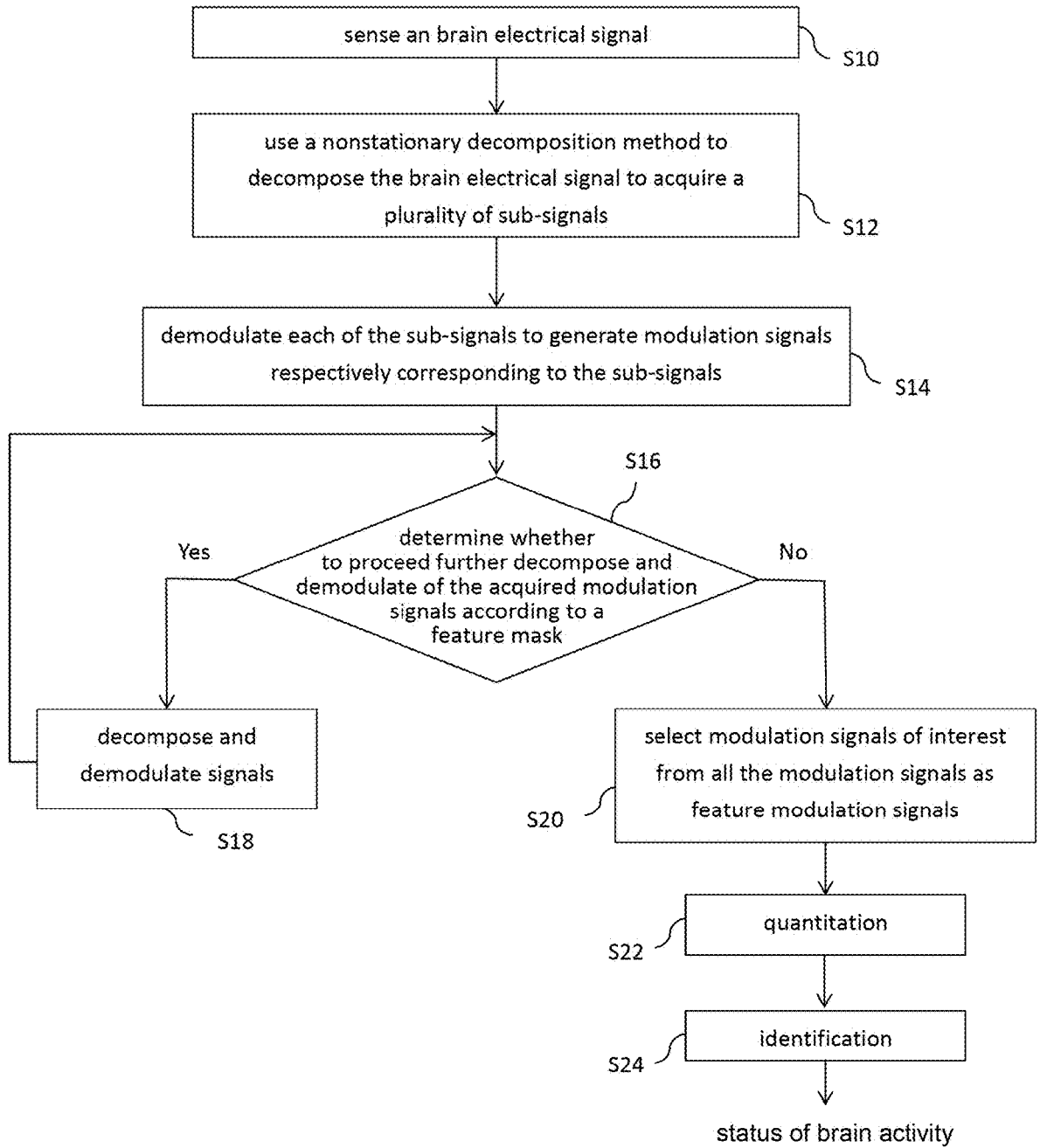
FIG. 2 is a flowchart of a brain activity analysis method according to one embodiment of the present invention.
Figure 3A:
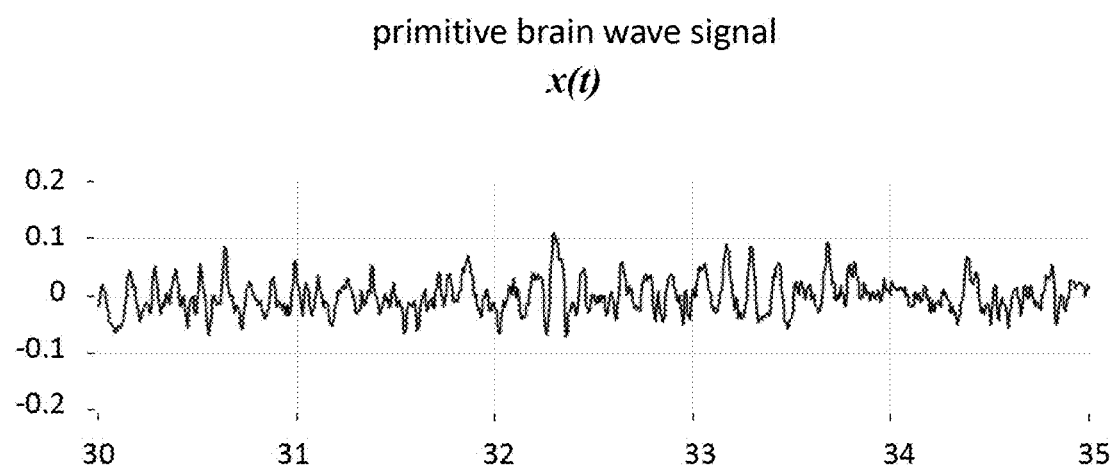
FIG. 3(a) is a diagram showing a primitive brain wave signal.

After the fundamental architecture of the apparatus of the present invention has been described above, the brain activity analysis method of the present invention will be fully described below. Refer to FIG. 2 a flowchart of a brain activity analysis method according to one embodiment of the present invention, and refer to FIG. 1 again. The brain activity analysis method of the present invention comprises Steps S10-S24. In Step S10, use the sensing unit 10 to measure the brain wave of at least one subject to acquire at least one brain electrical signal, as shown in FIG. 3(a). The brain electrical signal may be an electroencephalography (EEG) signal, an intracranial electroencephalogram (iEEG) signal, or an electrocorticography (ECoG) signal. The brain electrical signal is transmitted to the signal processing unit 12 and processed and analyzed in Steps S12-S24.

Figure 3B:
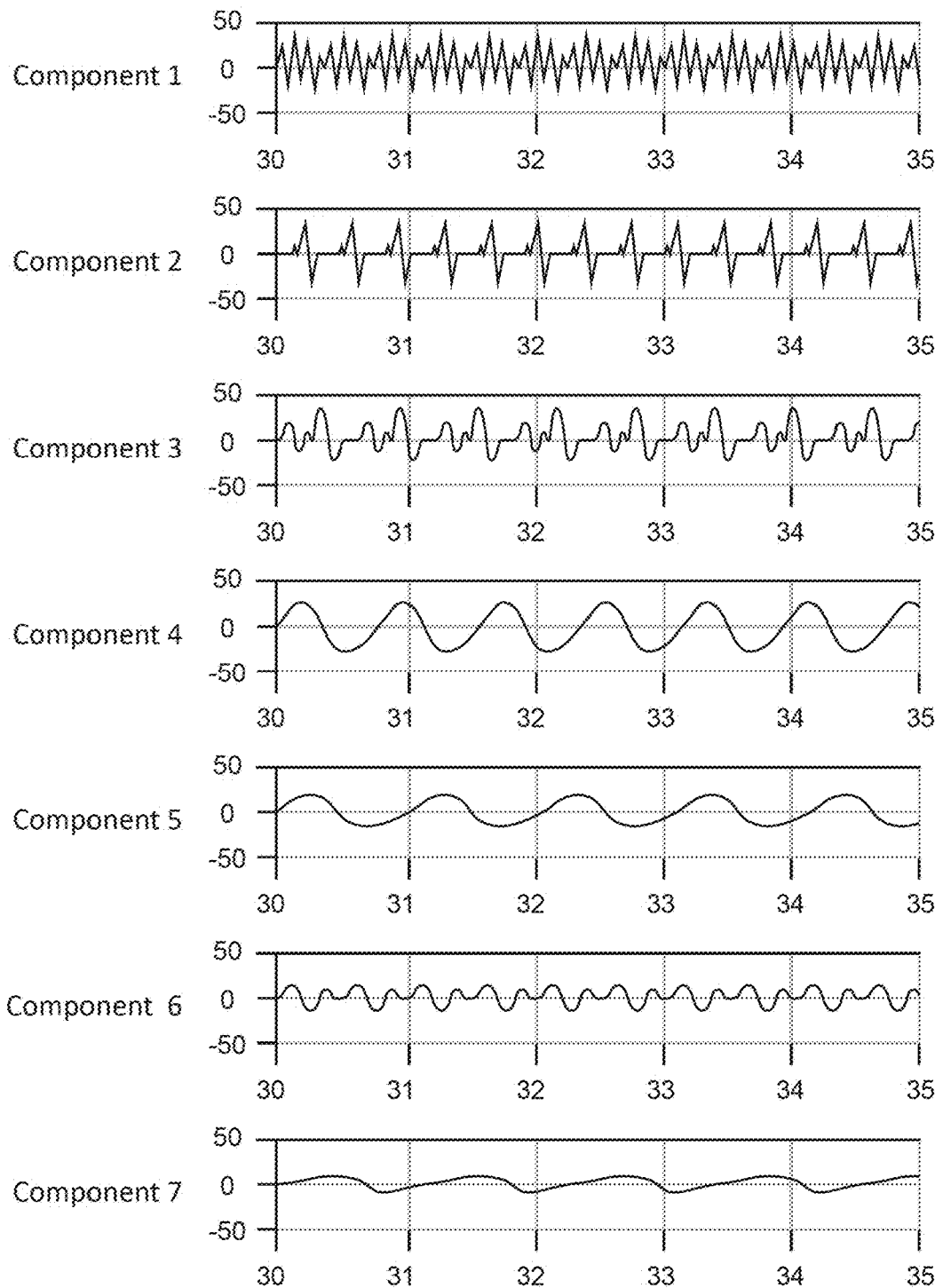
FIG. 3(b) is a diagram schematically showing that a brain electrical signal is decomposed into a plurality of sub-signals carrying intrinsic feature components according to one embodiment of the present invention.
Figure 3C:
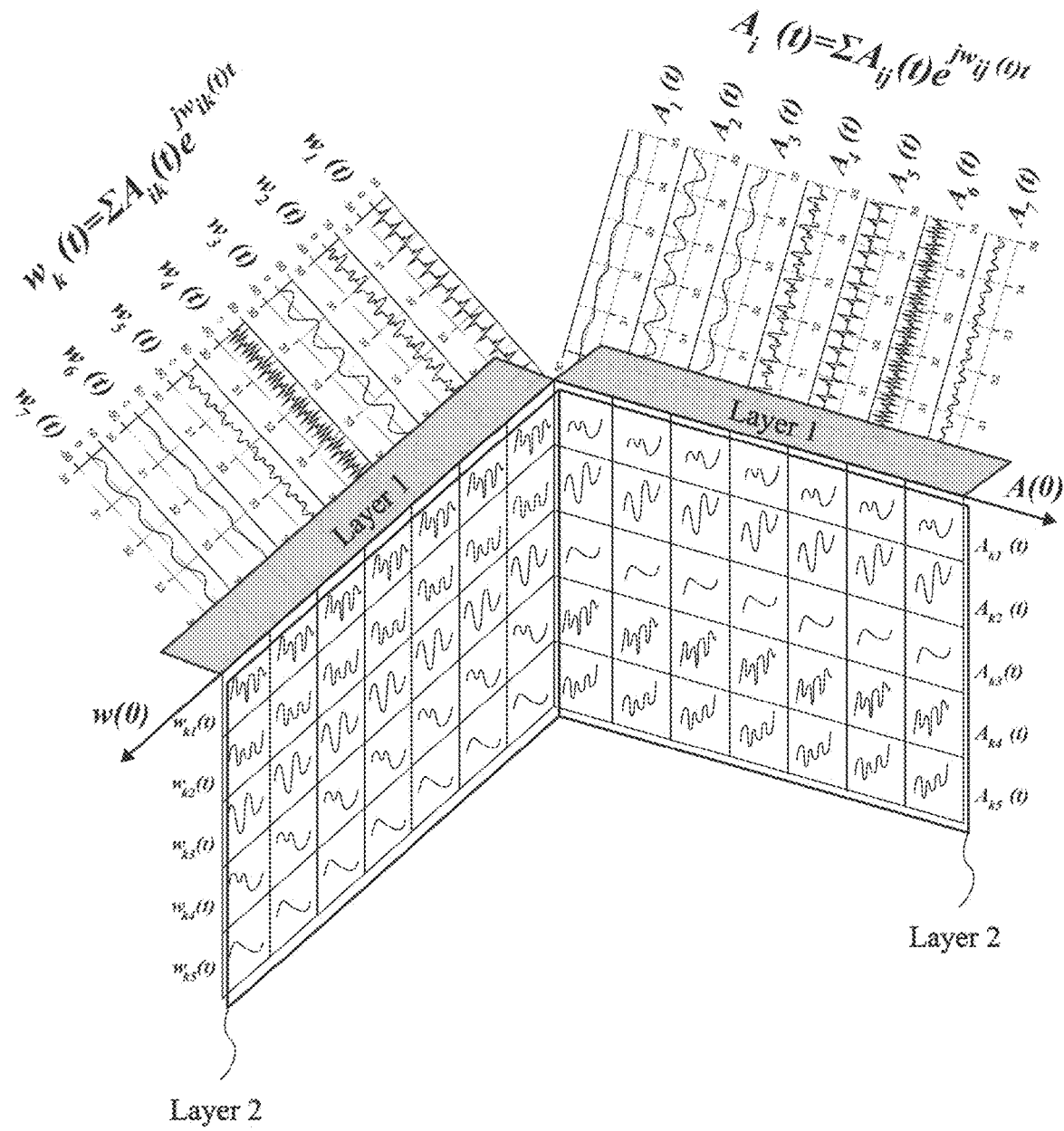
FIG. 3(c) is a diagram schematically showing that the sub-signals are demodulated into modulation signals each containing a frequency-modulation part and an amplitude-modulation part according to one embodiment of the present invention.
Figure 3D:
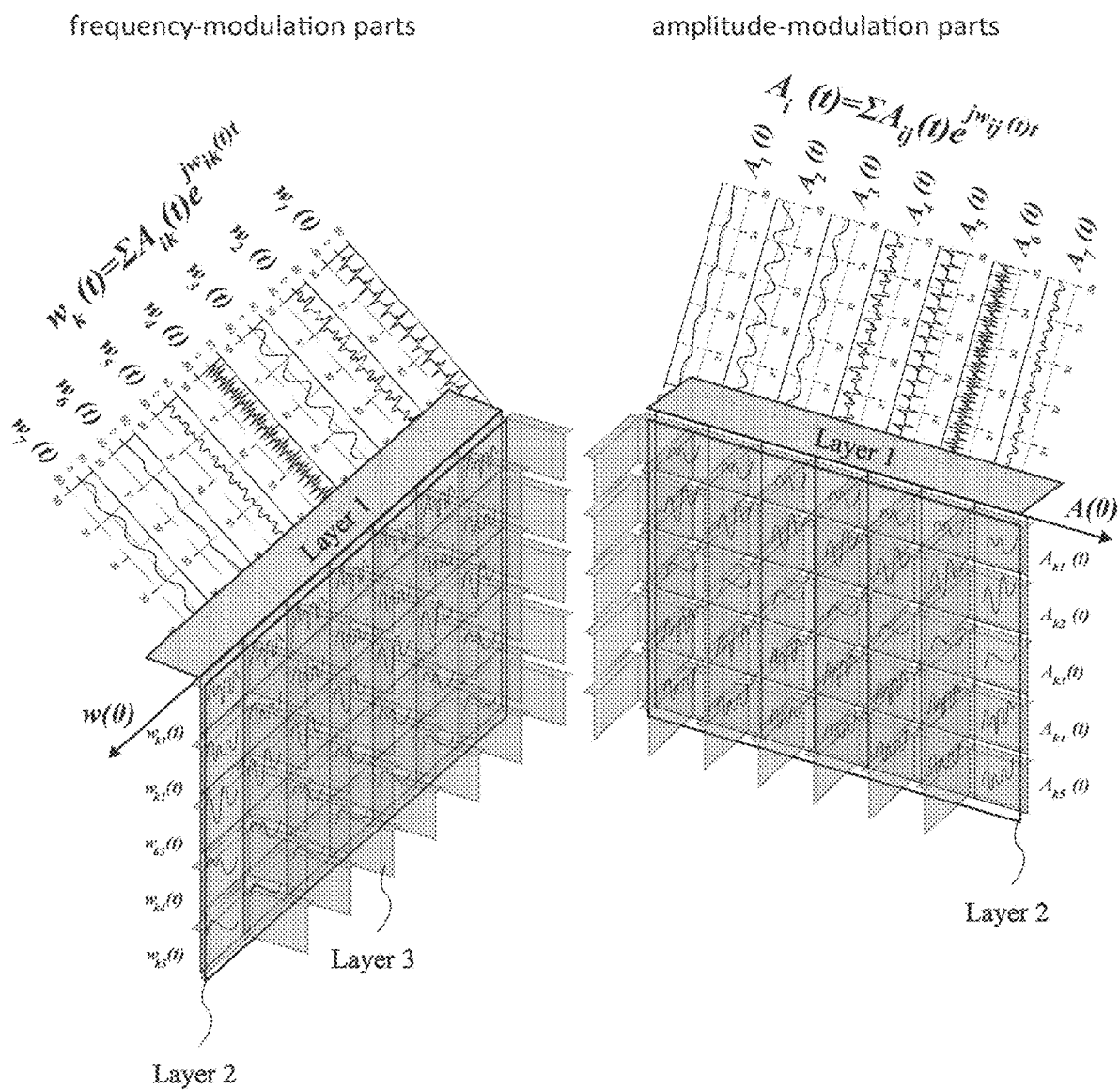
FIG. 3(d) is a diagram schematically showing the signals generated after decomposition and demodulation has been proceeded three times according to one embodiment of the present invention.

In Step S12, use a nonstationary decomposition method, such as the empirical mode decomposition (EMD) method, to decompose the brain electrical signal to acquire a plurality of sub-signals carrying intrinsic feature components, as Components 1-7 shown in FIG. 3(b). In Step S14, demodulate each of the sub-signals, wherein a normalization operation is used to decompose the sub-signals, which respectively carry different intrinsic feature components, to acquire modulation signals respectively corresponding to the sub-signals. The modulation signals include frequency-modulation parts and amplitude-modulation parts. The Layer 1 signal shown in FIG. 3(c) includes the frequency-modulation parts ($W_k(t)$, k=1-7) and the amplitude-modulation parts ($A_i(t)$, i=1-7), which are obtained via decomposing every sub-signal. In Step S16, perform recursive iteration, wherein a preset feature mask is used to determine whether to perform recursive iteration of the acquired modulation signal (including the frequency-modulation parts and the amplitude-modulation parts), i.e. determine whether to perform a further decomposition-demodulation process of the acquired signals. If no, the process directly proceeds to Step S20. If yes, the process proceeds to Step S18: continue decomposition and demodulation of the signals. The details of the decomposition and demodulation in Step S18 are respectively identical to Step S12 and Step S14. After Step S18 is completed, the process returns to Step S16 for determining whether to proceed a further decomposition-demodulation process of the signals until the number of decomposition and demodulation has reached the number determined by the feature mask. The number of recursive iteration (the number of decomposition and demodulation of signals) is exactly the number of the layers that the signal is decomposed into. The number of recursive iteration required to analyze the feature is dependent on the characteristics of the signal. In this embodiment, the components of Layer 1 are further decomposed and demodulated for the second time and the third time to generate the Layer 2 modulation signals shown in FIG. 3(c) and the Layer 3 modulation signals shown in FIG. 3(d).

Figure 3E:
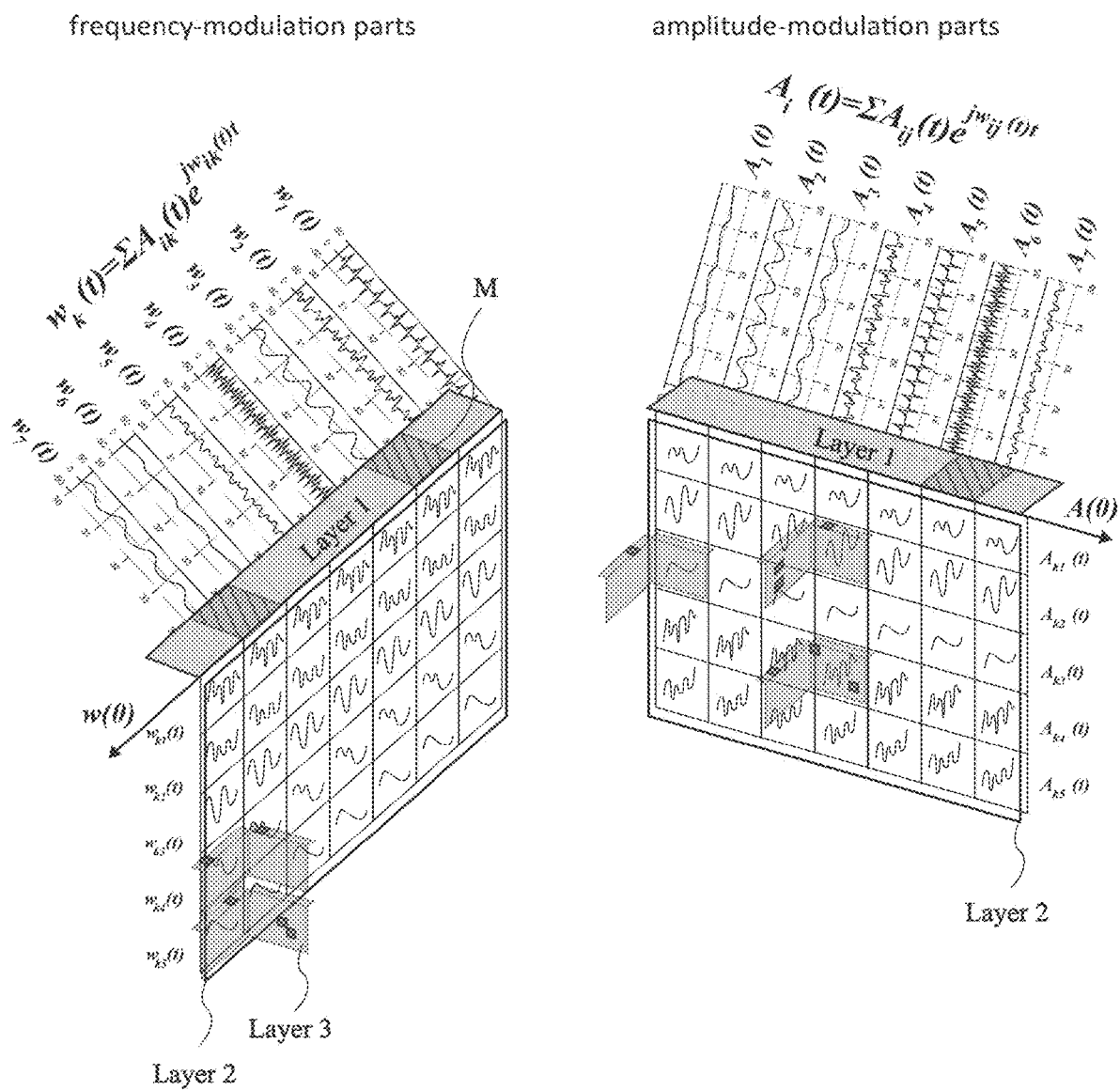
FIG. 3(e) is a diagram schematically showing the signals determined by a feature mask according to one embodiment of the present invention.
Figure 3F:
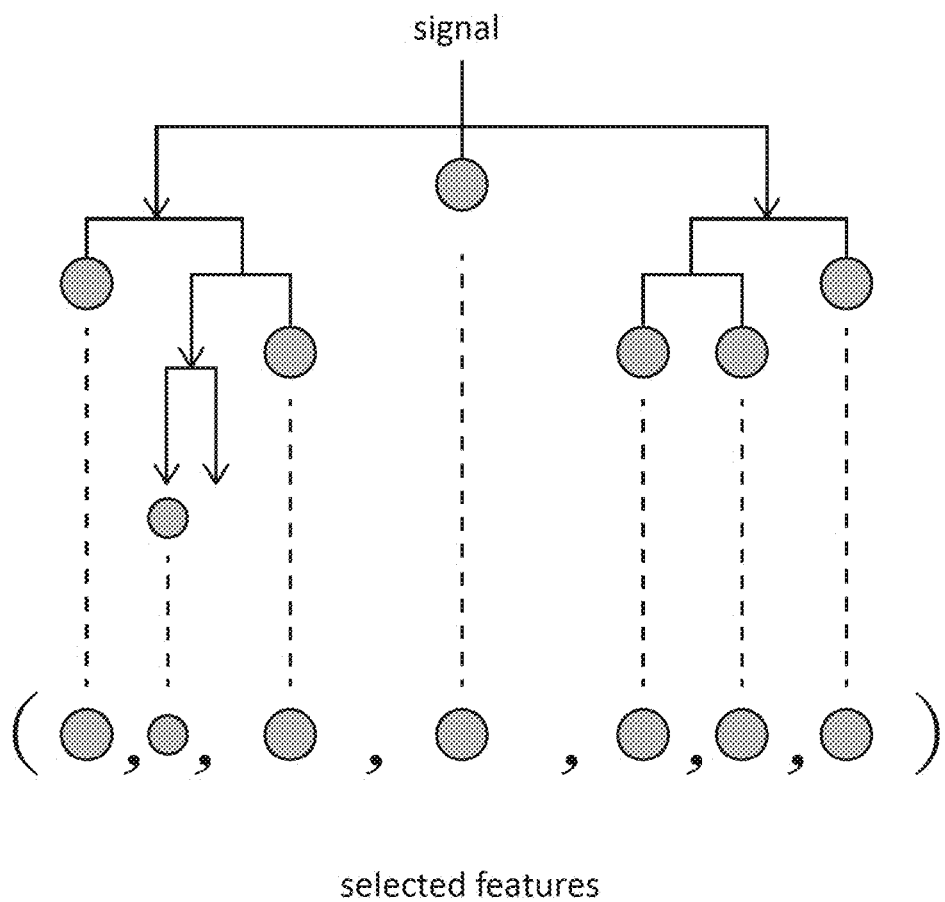
FIG. 3(f) is a diagram schematically showing that the modulation signals of interest are selected from all the modulation signals according to one embodiment of the present invention.

The number of recursive iteration and the signal features determine feature components. Therefore, in Step S20, set a feature mask M to determine the feature components. As shown in FIG. 3(e) and FIG. 3(f), the feature mask M is used to select modulation signals of interest as feature modulation signals from Layer 1 modulation signals, Layer 2 modulation signals and Layer 3 modulation signals. The feature modulation signals are to be used in the succeeding calculation to obtain the multidimensional variation of the intrinsic features of the brain wave. In Step S22, perform quantitation processes of the features of interest, such as calculation of power densities, instantaneous frequencies, or averaged periods of the features of interest. In Step S24, use a classification model to perform identification processes. The classification model is constructed according to the personal history and the pre-trained parameters. Thereby, the present invention can obtain the analysis result corresponding to the abovementioned brain electrical signal, i.e. the status of brain activity. After obtaining the status of brain activity, the signal processing unit 12 presents the result on the display unit 16.

Figure 4A:
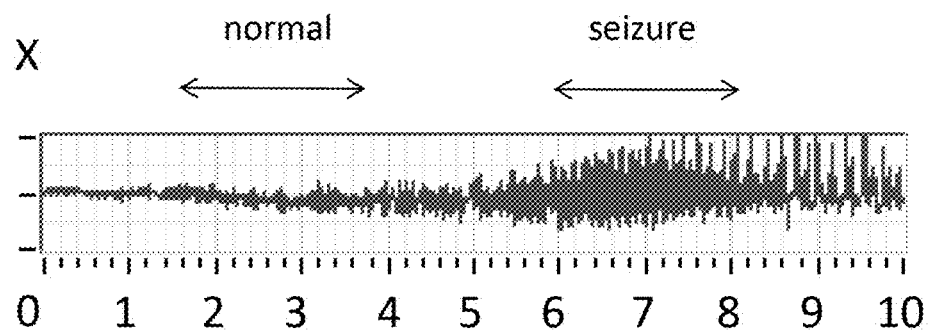
FIGS. 4(a)-4(e) are diagrams schematically showing the signals generated in sequential cycles of decomposing and demodulating the brain electrical signal measured during normal condition and seizure according to one embodiment of the present invention, wherein the feature mask is M=x (FM[2],AM[1(FM[1,2],AM[1,2]),2]).
Figure 4B:
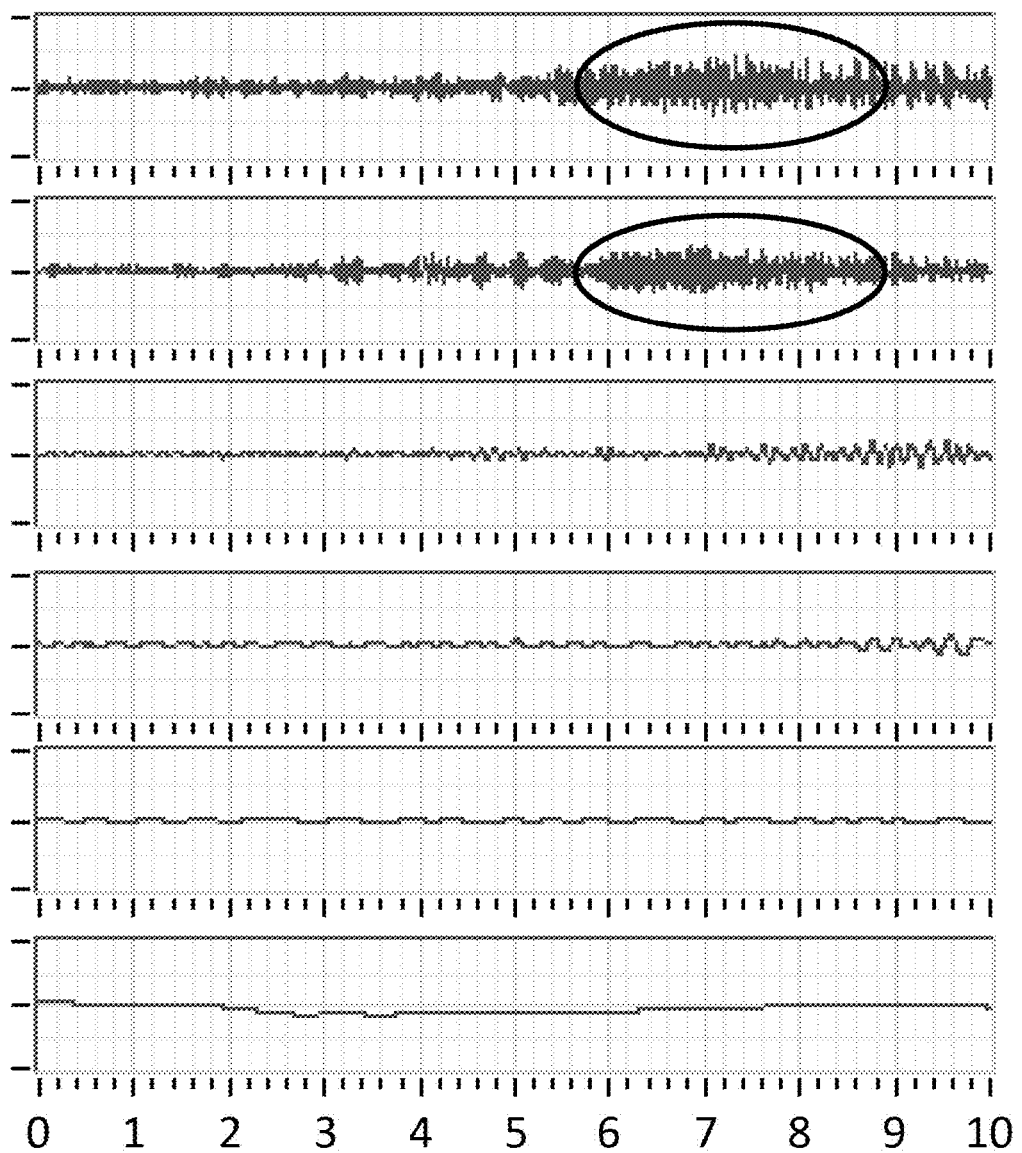
Figure 4C:
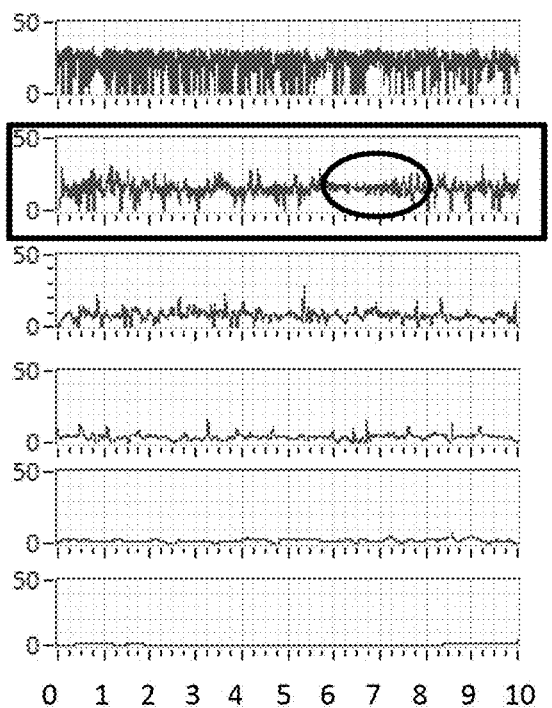
Figure 4C:
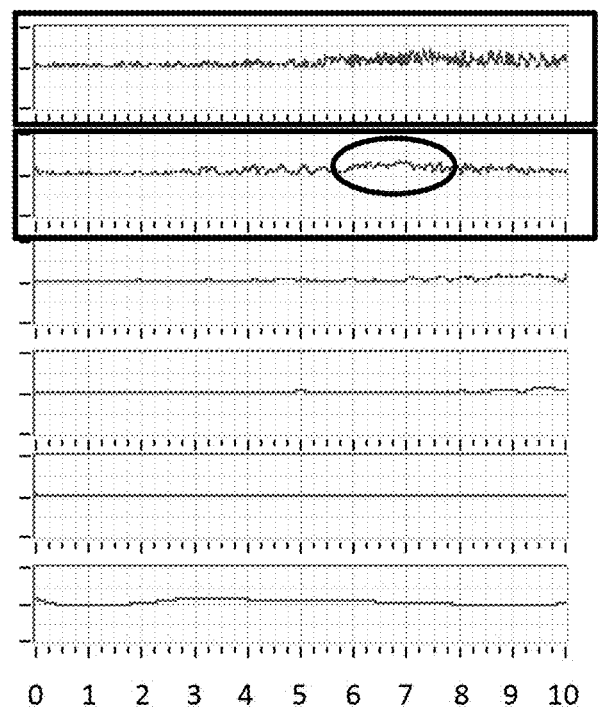
Figure 4D:
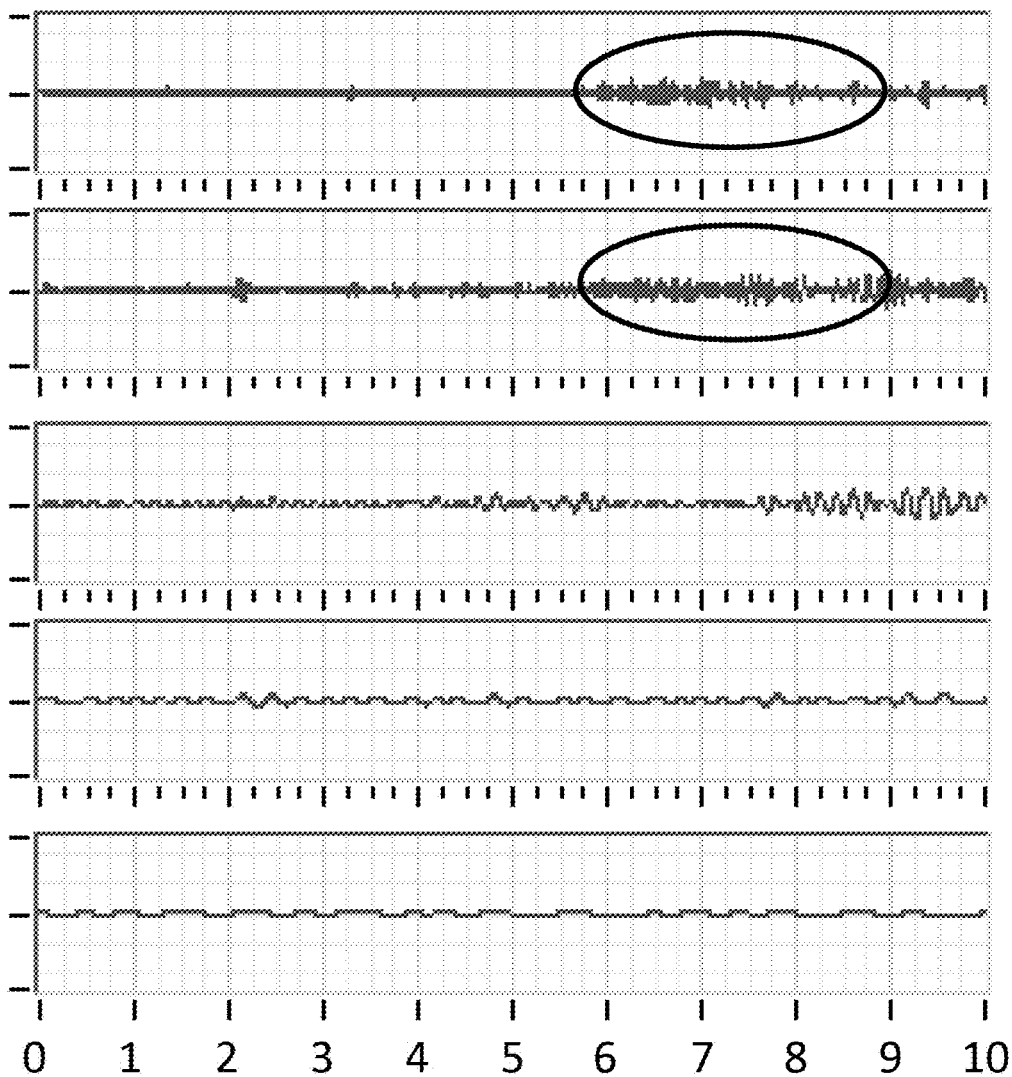
Figure 4E:
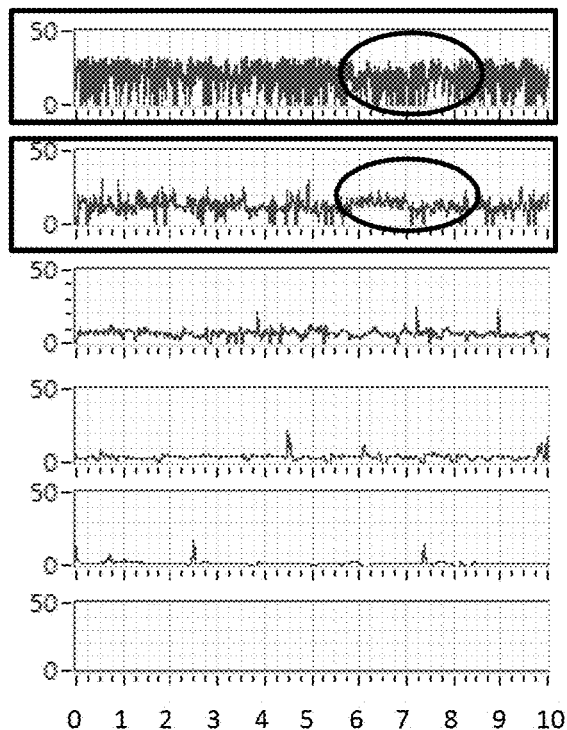
Figure 4E:
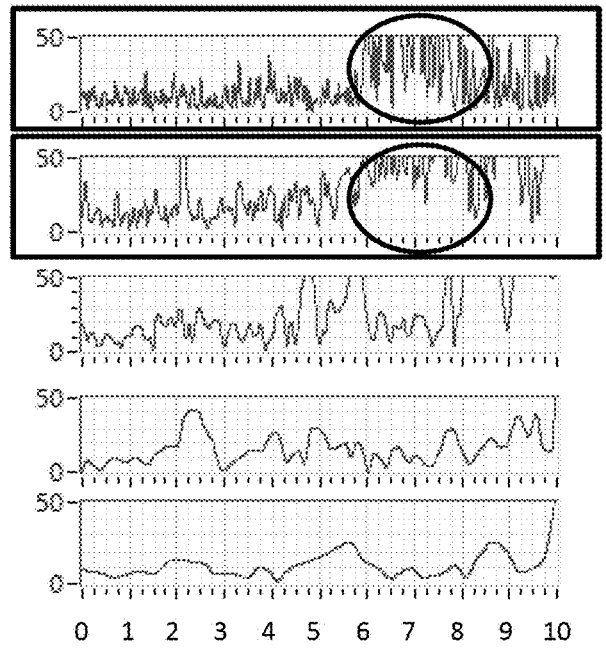

Succeeding to full demonstration of the spirit of the present invention, the example shown in FIG. 4(a) and FIG. 4(b) is used to illustrate the technical contents of the present invention. The encircled portions are the features selected by the feature mask M=x(FM[2],AM[1(FM[1,2],AM[1,2]),2]), wherein x denotes the brain electrical signal; the Arabic numerals 1, 2 denotes the sub-signals; AM denotes amplitude modulation; FM denotes frequency modulation. FIG. 4(a) shows the brain electrical signal detected in seizure. The signal in FIG. 4(a) is decomposed into a plurality of intrinsic feature sub-signals in a nonstationary decomposition method, as shown in FIG. 4(b). Each of the sub-signals in FIG. 4(b) is demodulated into a frequency-modulation part and an amplitude-modulation part, as shown in FIG. 4(c). The modulation signals x(FM[2]) and x(AM[1,2]) are selected as the features to be used in the succeeding calculation. The modulation signal x(AM[1]) is further decomposed to develop the intrinsic feature variation of the modulation signal, as shown in FIG. 4(d). Each of the signals in FIG. 4(d) is further demodulated into a frequency-modulation part and an amplitude-modulation part, as shown in FIG. 4(e). The modulation signals x(AM[1(FM[1,2])]) and x(AM[1(AM[1,2])]) are selected as the feature modulation signals to be used in the succeeding calculation. Thus, all the feature modulation signals of interest can be obtained according to the feature mask to implement the succeeding calculation.

In the present invention, the main application of the feature mask is to determine the number of decomposition and demodulation of signals and the positions of the selected feature modulation signals. The example described above uses a word string M=x(FM[2],AM[1(FM[1,2],AM[1,2]), 2]) to express the feature mask. However, the feature mask can also be expressed by a sequence matrix, wherein the odd-numbered matrix dimensions are the sequences of the post-decomposition sub-signals, and the even-numbered matrix dimensions are the sequences of the post-demodulation modulation signals, and wherein the number denotes the feature modulation signal selected by the matrix dimension. In the even-numbered matrix dimension, FM is arranged in the front, and AM is arranged in the rear. Thus, x(AM[1 (FM[1,2])]) and x(AM[1(AM[1,2])]) can be denoted by ([2], [([1, 2] [1, 2]), 2]).

In the present invention, the feature mask can also be expressed by a multidimensional matrix, such as a multidimensional Boolean matrix (abbreviated as T/F). The details thereof are stated below:

The first decomposition outputs three sub-signals of 1-dimensional sequences in form of [( ) ( ) ( )].

The demodulation converts the sub-signals into 2-dimensional sequences having two modulation parts in form of [([ ], [ ]) ([ ], [ ]) ([ ], [ ])] with FM arranged before and AM arranged behind, wherein x(FM[2]) is expressed by [([F], F]) ([T], [F]) ([F], [F])]; x(AM[1,2]) is expressed by [([F], [T]) ([F], [T]) ([F], [F])]; x(FM[2], AM[1,2]) is expressed by [([F], [T]) ([T], [T]) ([F], [F])].

The modulation component is decomposed into three sub-signals of 3-dimensional sequences in form of [([( ) ( ) ( )], [( ) ( ) ( )]) ([( ) ( ) ( )], [( ) ( ) ( )]) ([( ) ( ) ( )], [( ) ( ) ( )])].

Then, the iterative demodulation converts the sub-signals into 4-dimensional sequences having two modulation components in form of [([([ ], [ ]) ([ ], [ ]) ([ ], [ ])], [([ ], [ ]) ([ ], [ ]) ([ ], [ ])]) ([([ ], [ ]) ([ ], [ ]) ([ ], [ ])], [([ ], [ ]) ([ ], [ ]) ([ ], [ ])]) ([([ ], [ ]) ([ ], [ ]) ([ ], [ ])], [([ ], [ ]) ([ ], [ ])])] with FM arranged before and AM arranged behind.

A portion of the selected feature mask can be expressed as follows: x(AM[1(FM[1,2])]) is denoted by [([F], [([T], [F]) ([T], [F]) ([F], [F])]) ([F], [F]) ([F], [F])];
x(AM[1(AM[1,2])]) is denoted by [([F], [([F], [T]) ([F], [T]) ([F], [F])]) ([F], [F]) ([F], [F])].

In summary, x(FM[2], AM[1(FM[1,2], AM[1,2]), 2]) in the abovementioned example can be expressed by a multidimensional matrix denoted by [([F], [([T], [T]) ([T], [T]) ([F], [F])]) ([T], [T]) ([F], [F])].

In addition to involving the estimation of waveforms and frequency spectral analysis of the conventional technology, the present invention further provides calculations of intrinsic features, which are particularly useful for the multilayer neural network where many intrinsic features are not obvious in the primitive wave and the primitive frequency spectrum. The present invention not only presents variations of brain wave to enhance accuracy of the identification but also performs decomposition and analyzation with respect to different frequency modulations and amplitude modulations to form a multilayer and multidimensional feature space, which is sufficient to reveal nonstationary features of brain activity. Further, the feature mask used by the present invention can significantly reduce the complexity the conventional technology suffers in decomposing signals and effectively reduce the load in computation. Therefore, the present invention can greatly promote the practicability of brain wave-based diagnosis in neurological diseases.

The embodiments have been described above to demonstrate the technical contents and characteristics of the present invention and enable the persons skilled in the art to understand, make, and use the present invention. However, these embodiments are only to exemplify the present invention but not to limit the scope of the present invention. Any equivalent modification or variation according to the spirit of the present invention is to be included within the scope of the present invention.

What is claimed is:

1. A brain activity analysis apparatus for processing at least one brain electrical signal to generate an analysis result, said brain activity analysis apparatus comprising:
   at least one brain activity sensor, said brain activity sensor configured to detect brain waves of a subject to acquire said at least one brain electrical signal;
   a signal processor in communication with said brain activity sensor, said signal processor configured to:
      receive said brain electrical signal,
      use a nonstationary decomposition method to decompose said brain electrical signal to acquire a plurality of sub-signals carrying intrinsic feature components,
      demodulate each of said sub-signals to generate modulation signals respectively corresponding to said sub-signals,
      recursively iterate said nonstationary decomposition method to further decompose and demodulate said modulation signals according to a preset feature mask, said feature mask formed of a word string, a sequence matrix, or a multidimensional matrix,
      select signals of interest from said modulation signals as feature modulation signals according to said feature mask, and
      undertake quantitation processes and identification processes of said feature modulation signals to obtain an analysis result corresponding to said brain electrical signal; and
   a display electrically connected with said signal processor and configured to present said analysis result.

2. The brain activity analysis apparatus according to claim 1, wherein said brain electrical signal is an electroencephalography (EEG) signal, an intracranial electroencephalogram (iEEG) signal, or an electrocorticography (ECoG) signal.

3. The brain activity analysis apparatus according to claim 1, wherein said nonstationary decomposition method is an empirical mode decomposition (EMD) method.

4. The brain activity analysis apparatus according to claim 1, wherein a normalization operation is used to demodulate each of said sub-signals to obtain said modulation signals.

5. The brain activity analysis apparatus according to claim 1, wherein said modulation signals include frequency-modulation parts and amplitude-modulation parts.

6. The brain activity analysis apparatus according to claim 1, wherein said analysis result is a status of brain activity.

7. The brain activity analysis apparatus according to claim 1, wherein said quantitation processes include calculation of power densities, instantaneous frequencies, or averaged periods.

8. The brain activity analysis apparatus according to claim 1, wherein a classification model is used in said identification processes, and wherein said classification model involves personal history and pre-trained parameters.

9. The brain activity analysis apparatus according to claim 1 further comprising a storage unit electrically connected with said signal processor and configured to store signals, data and results processed by said signal processor.

* * * * *